(12) United States Patent
Sikora

(10) Patent No.: US 8,812,248 B2
(45) Date of Patent: Aug. 19, 2014

(54) SYSTEMS AND METHODS FOR GENOTYPING BY ANGLE CONFIGURATION SEARCH

(75) Inventor: Marcin Sikora, Foster City, CA (US)

(73) Assignee: Life Technologies Corporation, Carlsbad, CA (US)

( * ) Notice: Subject to any disclaimer, the term of this patent is extended or adjusted under 35 U.S.C. 154(b) by 516 days.

(21) Appl. No.: 13/083,361

(22) Filed: Apr. 8, 2011

(65) Prior Publication Data

US 2011/0252051 A1    Oct. 13, 2011

Related U.S. Application Data

(60) Provisional application No. 61/322,274, filed on Apr. 8, 2010.

(51) Int. Cl.
G06F 19/00 (2011.01)
G11C 17/00 (2006.01)
G06F 15/00 (2006.01)

(52) U.S. Cl.
USPC .................................. 702/20; 365/94; 700/1

(58) Field of Classification Search
None
See application file for complete search history.

(56) References Cited

U.S. PATENT DOCUMENTS

| 6,895,337 B1 | 5/2005 | Scholl et al. |
| 8,554,487 B2 * | 10/2013 | Kim et al. .................... 702/19 |
| 2008/0281529 A1 | 11/2008 | Tenenbaum et al. |

FOREIGN PATENT DOCUMENTS

| JP | 2005-276234 | 10/2005 |
| JP | 2006-065501 | 5/2006 |

OTHER PUBLICATIONS

PCT/US2011/031824, International Preliminary Report on Patentability—Written Opinion of the International Searching Authority, Dec. 23, 2011.

* cited by examiner

*Primary Examiner* — John S Brusca

(57) ABSTRACT

Methods and systems for the analysis of genotyping data are presented. According to various embodiments of methods and systems, an angle configuration search may be performed. In various embodiments, an exhaustive search over the entirety of an angle configuration space may be performed to provide a fit to a plurality of angles determined for a plurality of points in a data set generated from a plurality of biological samples. For various embodiments, the angle configuration space may be defined to ensure that a global fit may be determined. According to various methods and systems, a data base of possible angle configurations may be searched, in which each angle configuration may include three angles. According to various methods and systems, a data base of possible angle configurations may include for each angle configuration a probability that the angle configuration may occur.

23 Claims, 11 Drawing Sheets

SYSTEMS AND METHODS FOR GENOTYPING BY ANGLE CONFIGURATION SEARCH

BACKGROUND

Genotyping assays configured as a duplex reaction is well known in the art. In such a duplex reaction, two dyes having emissions at different wavelengths can be associated with each of a probe directed to one of two alleles of a target diploid genomic locus in a biological sample. In such duplex reactions, a discrete set of signals for each of three possible genotypes is produced by combinations of a first dye signal (signal 1) and a second dye signal (signal 2), which yield three discrete sets of signals given as (signal 1, signal 1), (signal 1, signal 2), and (signal 2, signal 2). Such signals may be collected as a data set that may include a plurality of data points, where each data point corresponds to one of the three discrete sets of signals for each sample in a plurality of samples. Such a data set of data points may be stored in a variety of computer readable media, and may be analyzed either dynamically during analysis or post analysis.

In that regard, the three discrete sets of signals that may be produced for each of three possible genotypes may be displayed in a Cartesian coordinate plot. The axes of such a plot may be displayed as a first dye signal versus a second dye signal, where each discrete set of signals for each sample may be represented as a data point in such a plot. Then, for a plurality of samples representative of a diploid genome, anywhere from 1-3 clusters of points may occur in such a Cartesian coordinate plot. Often, in such approaches, an angle in the Cartesian plot for each data point is determined, so that the data may be expressed in an angular format. Such data has typically been analyzed in the art by using cluster analysis to define discrete clusters, and assign a genotype based on cluster fit alone.

Such approaches may fail to accurately assign a genotype to a sample for a variety of reasons. First, the angle configuration of the three angles for a variety of genotype assays may be significantly different and additionally, the angle configuration may vary from run-to-run for any particular genotype assay. In that regard, the angle information alone is not sufficient to assign a genotype. Second, for a plurality of biological samples analyzed, it is possible to have the data clustered in only one or two clusters. For data in which all three clusters are present, a fit to a model may be more easily achieved, as the angle space is bounded by three possible solutions. However, for data sets obtained from a plurality of biological samples in which only one or two clusters occur, a fit to a model may be more difficult, resulting in incorrect genotype calls to be made for at least some samples. For example, a final call in such data sets may depend on the angle of a control sample. In that regard, if the control sample is contaminated, for example, or in any way falsely identified with an incorrect cluster, erroneous calls will be made for every member of that cluster.

There is a need in the art for a robust analysis of genotype data, in which the optimization is well-defined, and yields a suitable confidence in a final result of assignment of genotype for samples in data sets, where the data sets may be represented by a finite number of clusters of data points based on the ploidy state of the genome of an organism.

DETAILED DESCRIPTION

The present teachings relate to embodiments of methods and systems for the analysis of genotyping data. According to various embodiments of methods and systems, an angle configuration search may be performed. In various embodiments, an exhaustive search over the entirety of an angle configuration space may be performed to provide a fit to a plurality of angles determined for a plurality of data points in a data set generated from a plurality of biological samples. For various embodiments, the angle configuration space may be defined to ensure that a global fit may be determined. According to various methods and systems, a data base of possible angle configurations may be searched, in which each angle configuration includes three angles. According to various methods and systems, a data base of possible angle configurations may include for each angle configuration a probability that the angle configuration may occur. For various embodiments of methods and systems for the analysis of genotyping data, preprocessing of the data may be done before the angle configuration search may be performed. Additionally, a quality score may be assigned to a genotype call made for a sample, using various embodiments of methods and systems for the analysis of genotyping data.

Figure 3:
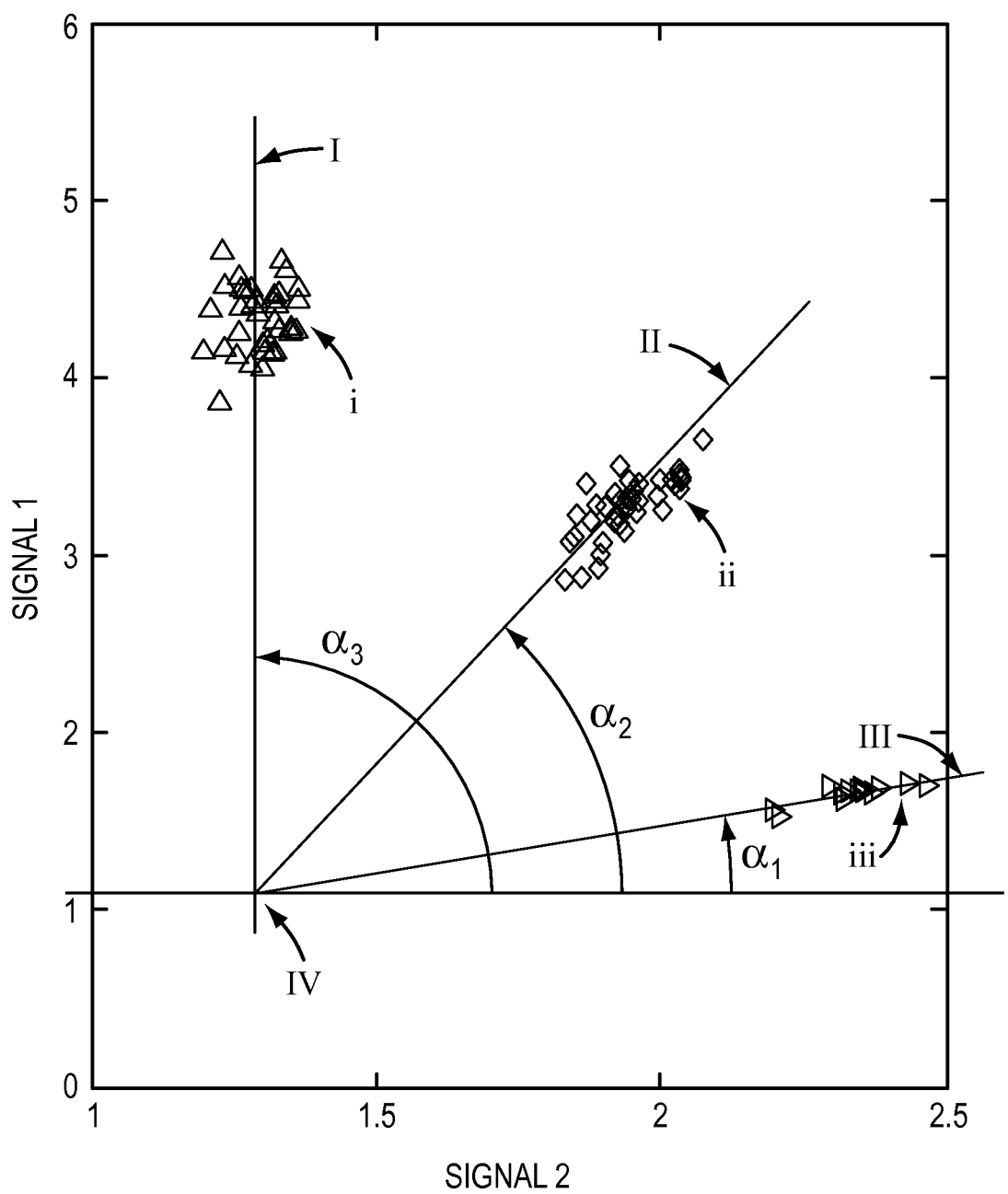
FIG. 3 is an exemplary representation of the assignment of an angle to clusters of data, according to various embodiments of methods for the analysis of genotyping data.

Various embodiments of methods and systems according to the present teachings may utilize data sets that may be represented according to the graph depicted in FIG. 3. Such a representation may arise from analyses utilizing two dyes having emissions at different wavelengths, which dyes can be associated with each of a probe directed at one of two alleles of a diploid genomic locus in a biological sample. In such duplex reactions, a discrete set of signals for each of three possible genotypes is produced. In a Cartesian coordinate system of signal 1 versus signal 2, as shown in FIG. 3, each data point shown on such a graphic representation may have coordinates in one of three discrete sets of signals given, for example in reference to FIG. 3, as (signal 1, signal 1), (signal 1, signal 2), and (signal 2, signal 2). As previously described, each discrete set of signals for a plurality of samples may be stored as data points in a data set. Such data sets may be stored in a variety of computer readable media, and analyzed either dynamically during analysis or post analysis, as will be discussed in more detail subsequently. One such type of assay used to demonstrate the features of embodiments of methods and systems for the analysis of genotyping data can utilize TaqMan® reagents, and may use FAM and VIC dye labels. However, one of ordinary skill in the art will recognize that a variety of assays including labeling probe reagents may be utilized to produce data that may be analyzed according to various embodiments of methods and systems of the present teachings.

The term "labeling probe" generally, according to various embodiments, refers to a molecule used in an amplification reaction, typically for quantitative or real-time PCR analysis, as well as end-point analysis. Such labeling probes may be used to monitor the amplification of the target polynucleotide. In some embodiments, oligonucleotide probes present in an amplification reaction are suitable for monitoring the amount of amplicon(s) produced as a function of time. Such oligonucleotide probes include, but are not limited to, the 5'-exonuclease assay TaqMan® probes described herein (see also U.S. Pat. No. 5,538,848), various stem-loop molecular beacons (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355,421 and 6,593,091), linear PNA beacons (see, e.g., Kubista et al., 2001, SPIE 4264:53-58), non-FRET probes (see, e.g., U.S. Pat. No. 6,150,097), Sunrise®/Amplifluor® probes (U.S. Pat. No. 6,548,250), stem-loop and duplex Scorpion™ probes (Solinas et al., 2001, Nucleic Acids Research 29:E96 and U.S. Pat. No. 6,589,743), bulge loop probes (U.S. Pat. No. 6,590, 091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Labeling probes can also comprise black hole quenchers (Biosearch), Iowa Black (IDT), QSY quencher (Molecular Probes), and Dabsyl and Dabcel sulfonate/carboxylate Quenchers (Epoch). Labeling probes can also comprise two probes, wherein for example a fluorophore is on one probe, and a quencher on the other, wherein hybridization of the two probes together on a target quenches the signal, or wherein hybridization on target alters the signal signature via a change in fluorescence. Labeling probes can also comprise sulfonate derivatives of fluorescenin dyes with a sulfonic acid group instead of the carboxylate group, phosphoramidite forms of fluorescein, phosphoramidite forms of CY 5 (available for example from Amersham).

As used herein, the term "nucleic acid sample" refers to nucleic acid found in biological samples according to the present teachings. It is contemplated that samples may be collected invasively or noninvasively. The sample can be on, in, within, from or found in conjunction with a fiber, fabric, cigarette, chewing gum, adhesive material, soil or inanimate objects. "Sample" as used herein, is used in its broadest sense and refers to a sample containing a nucleic acid from which a gene target or target polynucleotide may be derived. A sample can comprise a cell, chromosomes isolated from a cell (e.g., a spread of metaphase chromosomes), genomic DNA, RNA, cDNA and the like. Samples can be of animal or vegetable origins encompassing any organism containing nucleic acid, including, but not limited to, plants, livestock, household pets, and human samples, and can be derived from a plurality of sources. These sources may include, but are not limited to, whole blood, hair, blood, urine, tissue biopsy, lymph, bone, bone marrow, tooth, amniotic fluid, hair, skin, semen, anal secretions, vaginal secretions, perspiration, saliva, buccal swabs, various environmental samples (for example, agricultural, water, and soil), research samples, purified samples, and lysed cells. It will be appreciated that nucleic acid samples containing target polynucleotide sequences can be isolated from samples from using any of a variety of sample preparation procedures known in the art, for example, including the use of such procedures as mechanical force, sonication, restriction endonuclease cleavage, or any method known in the art.

The terms "target polynucleotide," "gene target", "target genomic locus" and the like as used herein are used interchangeably herein and refer to a particular nucleic acid sequence of interest. The "target" can be a polynucleotide sequence that is sought to be amplified and can exist in the presence of other nucleic acid molecules or within a larger nucleic acid molecule. The target polynucleotide can be obtained from any source, and can comprise any number of different compositional components. For example, the target can be nucleic acid (e.g. DNA or RNA). The target can be methylated, non-methylated, or both. Further, it will be appreciated that "target" used in the context of a particular nucleic acid sequence of interest additionally refers to surrogates thereof, for example amplification products, and native sequences. In some embodiments, a particular nucleic acid sequence of interest is a short DNA molecule derived from a degraded source, such as can be found in, for example, but not limited to, forensics samples. A particular nucleic acid sequence of interest of the present teachings can be derived from any of a number of organisms and sources, as recited above. Regarding the ploidy state of a target genomic locus, for an organism with a diploid genome, in which two alleles define a locus, that there are three possible genotypes for such a diploid state. One of ordinary skill in the art will appreciate that any ploidy state is discretely associated with a finite number of allelic combinations defining a genotype classification. Thus, for any ploidy state for any sample having a target genomic locus of interest, there are a finite and calculable number of genotypes.

As used herein, "DNA" refers to deoxyribonucleic acid in its various forms as understood in the art, such as genomic DNA, cDNA, isolated nucleic acid molecules, vector DNA, and chromosomal DNA. "Nucleic acid" refers to DNA or RNA in any form. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or free of chemical precursors or other chemicals when chemically synthesized.

Figure 4:
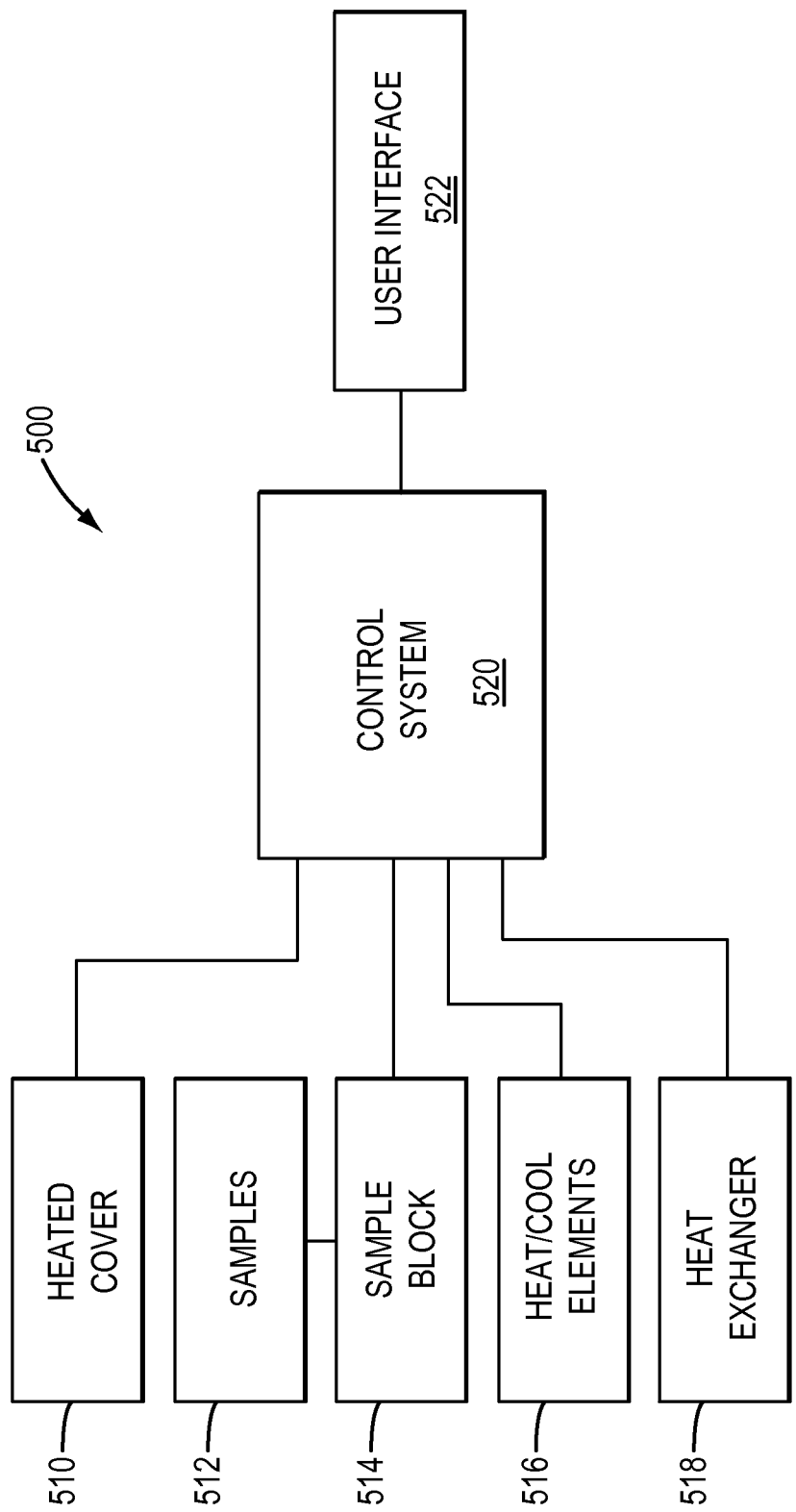
FIG. 4 is a block diagram of a PCR instrument that may be utilized to process samples analyzed for genotype.
Figure 5:
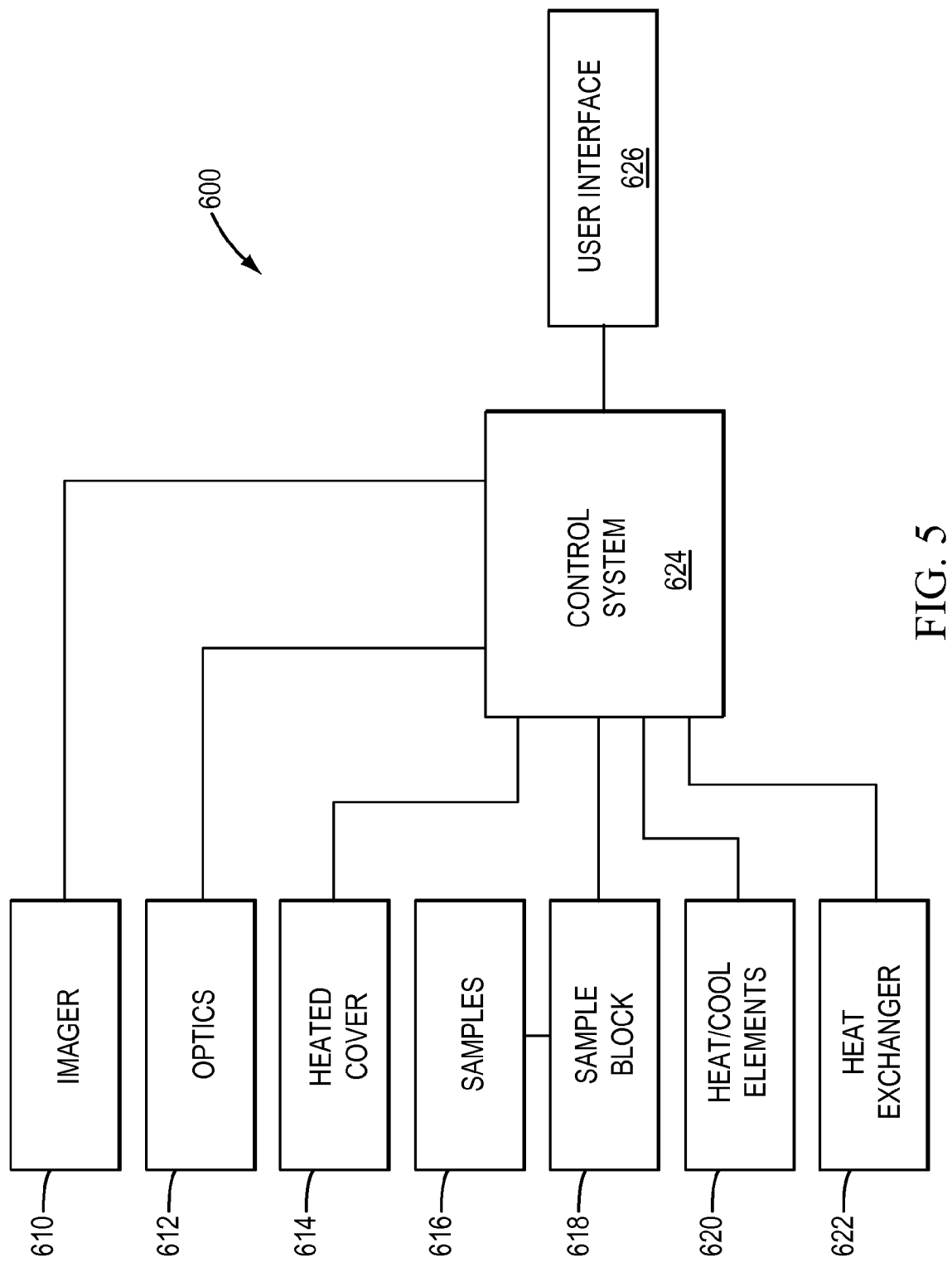
FIG. 5 is a block diagram of a PCR instrument that may be utilized to process samples analyzed for genotype.

Various embodiments of methods and systems for the analysis of genotyping data according to the present teachings may utilize various embodiments of a thermal cycler instrument as depicted in the block diagrams shown in FIG. 4 and FIG. 5.

According to various embodiments of a thermal cycler instrument 500, as shown in FIG. 4, a thermal cycling instrument may include a heated cover 510 that is placed over a plurality of samples 512 contained in a sample support device. In various embodiments, a sample support device may be a glass or plastic slide with a plurality of sample regions, which sample regions have a cover between the sample regions and heated lid 512. Some examples of a sample support device may include, but are not limited by, a multi-well plate, such as a standard microtiter 96-well, a 384-well plate, a micro device capable of processing thousands of samples per analysis, such as microfluidic device, such as a microcard, or a micro chip, or any variety of devices fabricated from a substantially planar support, such as a glass or plastic slide. The sample regions in various embodiments of a sample support device may include depressions, indentations, ridges, and combinations thereof, patterned in regular or irregular arrays formed on the surface of the substrate. In various embodiments of a thermal cycler instrument, include a sample block 514, elements for heating and cooling 516, and a heat exchanger 518. Various embodiments of a thermal block assembly according to the present teachings comprise components 514-518 of thermal cycler system 500 of FIG. 4.

Figure 6:
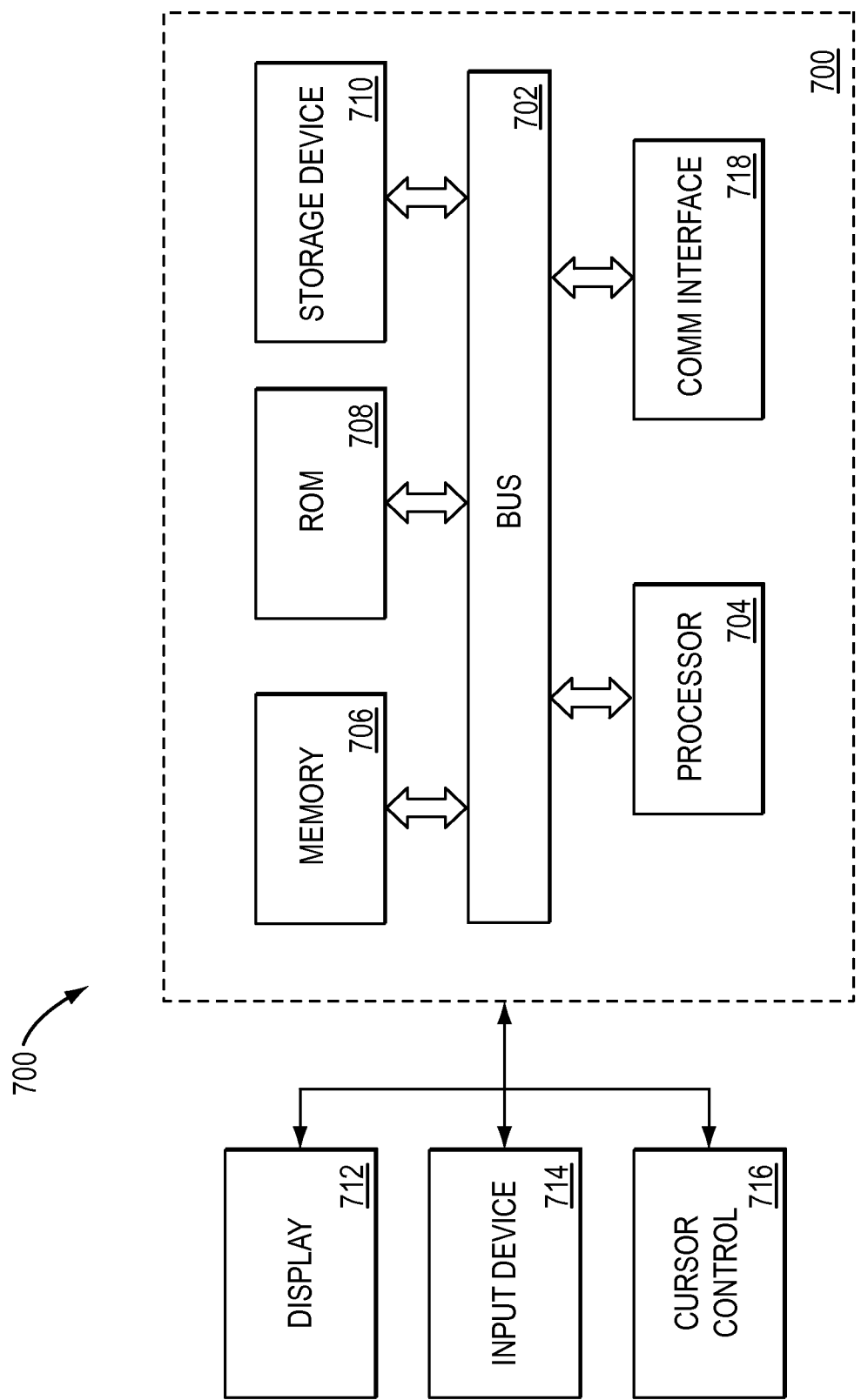
FIG. 6 is a block diagram that illustrates components of an exemplary computer system that may be utilized in the control and interface of PCR instrumentation.

In FIG. 5, various embodiments of a thermal cycling system 600 have the components of embodiments of thermal cycling instrument 500, and additionally a detection system, providing that real-time for various embodiment of FIG. 5. In contrast, for various embodiments of a thermal cycler of FIG. 4, detection is done as endpoint, or post-thermal cycling detection. A detection system may have an illumination source that emits electromagnetic energy, and a detector or imager 610, for receiving electromagnetic energy from samples 616 in sample support device. For embodiments of thermal cycler instrumentation 500 and 600, a control system 530 and 624, respectively, may be used to control the functions of the detection, heated cover, and thermal block assembly. The control system may be accessible to an end user through user interface 522 of thermal cycler instrument 500 and 626 of thermal cycler instrument 600. A computer system 700, as depicted in FIG. 6 may serve as to provide the control the function of a thermal cycler instrument, as well as the user interface function. Additionally, computer system 700 may provide data processing, display and report preparation functions. All such instrument control functions may be dedicated locally to the thermal cycler instrument, or computer system 700 may provide remote control of part or all of the control, analysis, and reporting functions, as will be discussed in more detail subsequently.

FIG. 6 is a block diagram that illustrates a computer system 700 that may be employed to carry out processing functionality, according to various embodiments, upon which embodiments of a thermal cycler system 500 of FIG. 4 or a thermal cycler system 600 of FIG. 5 may utilize. Computing system 700 can include one or more processors, such as a processor 704. Processor 704 can be implemented using a general or special purpose processing engine such as, for example, a microprocessor, controller or other control logic. In this example, processor 704 is connected to a bus 702 or other communication medium.

Further, it should be appreciated that a computing system 700 of FIG. 6 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 700 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 700 may include bus 702 or other communication mechanism for communicating information, and processor 704 coupled with bus 702 for processing information.

Computing system 700 also includes a memory 706, which can be a random access memory (RAM) or other dynamic memory, coupled to bus 702 for storing instructions to be executed by processor 704. Memory 706 also may be used for storing temporary variables or other intermediate information during execution of instructions to be executed by processor 704. Computing system 700 further includes a read only memory (ROM) 708 or other static storage device coupled to bus 702 for storing static information and instructions for processor 704.

Computing system 700 may also include a storage device 710, such as a magnetic disk, optical disk, or solid state drive (SSD) is provided and coupled to bus 702 for storing information and instructions. Storage device 710 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 710 may include other similar instrumentalities for allowing computer programs or other instructions or data to be loaded into computing system 700. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 710 to computing system 700.

Computing system 700 can also include a communications interface 718. Communications interface 718 can be used to allow software and data to be transferred between computing system 700 and external devices. Examples of communications interface 718 can include a modem, a network interface (such as an Ethernet or other NIC card), a communications port (such as for example, a USB port, a RS-232C serial port), a PCMCIA slot and card, Bluetooth, and the like. Software and data transferred via communications interface 718 are in the form of signals which can be electronic, electromagnetic, optical or other signals capable of being received by communications interface 718. These signals may be transmitted and received by communications interface 718 via a channel such as a wireless medium, wire or cable, fiber optics, or other communications medium. Some examples of a channel include a phone line, a cellular phone link, an RF link, a network interface, a local or wide area network, and other communications channels.

Computing system 700 may be coupled via bus 702 to a display 712, such as a cathode ray tube (CRT) or liquid crystal display (LCD), for displaying information to a computer user. An input device 714, including alphanumeric and other keys, is coupled to bus 702 for communicating information and command selections to processor 704, for example. An input device may also be a display, such as an LCD display, configured with touch screen input capabilities. Another type of user input device is cursor control 716, such as a mouse, a trackball or cursor direction keys for communicating direction information and command selections to processor 704 and for controlling cursor movement on display 712. This input device typically has two degrees of freedom in two axes, a first axis (e.g., x) and a second axis (e.g., y), that allows the device to specify positions in a plane. A computing system 700 provides data processing and provides a level of confidence for such data. Consistent with certain implementations of embodiments of the present teachings, data processing and confidence values are provided by computing system 700 in response to processor 704 executing one or more sequences of one or more instructions contained in memory 706. Such instructions may be read into memory 706 from another computer-readable medium, such as storage device 710. Execution of the sequences of instructions contained in memory 706 causes processor 704 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 704 for execution. Such instructions, generally referred to as "computer program code" (which may be grouped in the form of computer programs or other groupings), when executed, enable the computing system 700 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 710. Volatile media includes dynamic memory, such as memory 706. Transmission media includes coaxial cables, copper wire, and fiber optics, including the wires that comprise bus 702.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 704 for execution. For example, the instructions may initially be carried on magnetic disk of a remote computer. The remote computer can load the instructions into its dynamic memory and send the instructions over a telephone line using a modem. A modem local to computing system 700 can receive the data on the telephone line and use an infra-red transmitter to convert the data to an infra-red signal. An infra-red detector coupled to bus 702 can receive the data carried in the infra-red signal and place the data on bus 702. Bus 702 carries the data to memory 706, from which processor 704 retrieves and executes the instructions. The instructions received by memory 706 may optionally be stored on storage device 710 either before or after execution by processor 704.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

As previously discussed, reference is made to FIG. 3, which displays an idealized plot of data according to various embodiments of the present teachings. As one of ordinary skill in the art is apprised, for various embodiments of genotyping assays, a first probe directed to a first allele of a target diploid genomic locus, designated for exemplification as allele A, may have a first dye associated with the probe. Similarly, a second probe with a second dye may be directed to a second allele of a genomic locus, designated for exemplification as allele B. As amplification occurs during thermal cycling, for a biological sample homozygous in A, a set of signals of the first dye will be reported for each allele, for homozygous AA. Similarly, for a biological sample homozygous in B, a set of signals of the second dye will be reported for each allele of homozygous BB. Finally, for a biological sample heterozygous, a set of signals of a signal for the first dye and a signal for the second dye will be reported for heterozygous AB.

In that regard, various embodiments of genotyping assays so designed yield a discrete set of signals for each of the three possible allelic combinations of a target diploid genomic locus, as shown in FIG. 3, which displays three clusters of data points. Regarding step 10, of FIG. 1, and in reference to FIG. 3, each data point represents a discrete set of signals detected for a sample in a plurality of biological samples assayed for a genotype. As previously discussed, each data point shown in FIG. 3 may have coordinates in one of three discrete sets of signals given as (signal 1, signal 1), (signal 1, signal 2), and (signal 2, signal 2). For thermal cycle instruments, such as depicted in FIG. 4, after the samples are cycled to the last cycle, detection may be done as a post endpoint read. For thermal cycle instruments, such as depicted in FIG. 5, detection may occur dynamically in real-time as the samples are cycled to the last cycle and detection may additionally be done as a post endpoint read.

Figure 1:
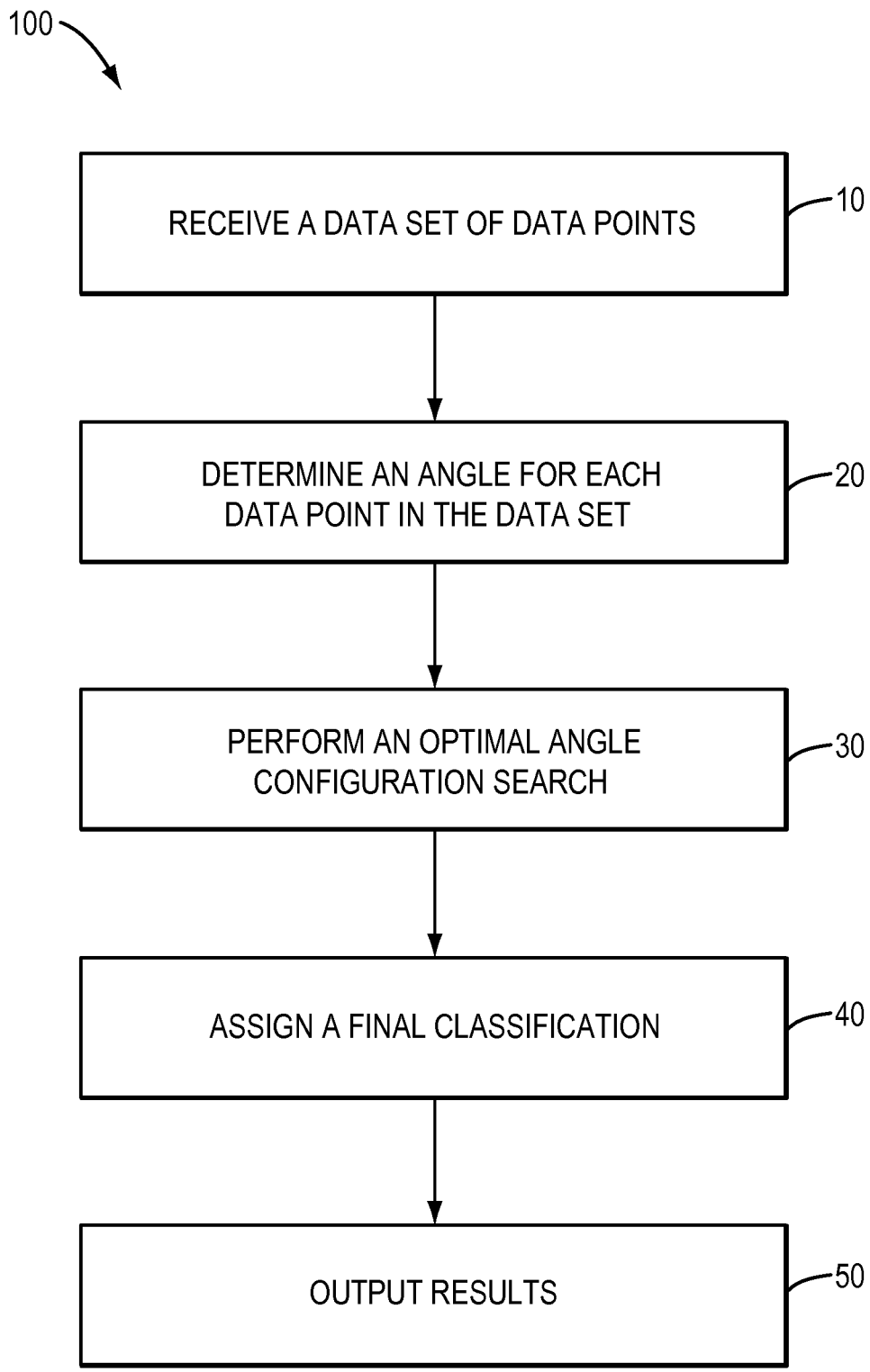
FIG. 1 is a flow chart that depicts various embodiments of methods for the analysis of genotyping data.

With reference to step 20 of FIG. 1, and as shown in FIG. 3, a baseline for establishing angles for the each data point may be constructed for a line represented by y=C, where C is a constant, and as shown in FIG. 3, contains a defined origin for the data. The origin (IV), as shown in FIG. 3, is a vertex for each angle, $\alpha_1$, $\alpha_2$, and $\alpha_3$. According to various embodiments of the present teachings, each data point in each cluster, i, ii, and iii of FIG. 3 may have an angle determined by a line constructed using a data point and a defined origin. According to various embodiments of the present teachings, the collective set of lines I, II, and III, associated with angles, $\alpha_3$, $\alpha_2$, and $\alpha_1$, respectively, constitute an angle configuration that may be selected from a data base of angle configurations, which will be discussed in more detail subsequently.

According to various embodiments, an origin may be defined by a negative control. A negative control may be referred to as a non-template control (NTC), which is a sample not containing the target genomic locus of interest. For various embodiments of a genotyping assay, the negative control or NTC may contain no oligonucleotide material, and may contain, for example, but not limited by, all the reagents brought to a volume equal to biological samples being assayed. According to other embodiments of a genotyping assay, the NTC may contain, for example, but not limited by, an oligonucleotide sample validated not to contain the sequences of a target genomic locus being assayed. As one of ordinary skill in the art is apprised, such NTC samples may still produce a background signal that may be detected. In that regard, one or more NTC samples may be used to define an origin as well as a baseline from which the angles of the samples emitting a discrete set of signals for each of three possible allelic can be determined. In various embodiments, a plurality of NTC samples may be used to determine an origin and a baseline thereby. As one of ordinary skill in the art is apprised, there may be a variety of ways to process the data from a plurality of NTC samples to determine a value for the origin, including, but not limited by, the determination of the mean, the median, and the centroid of a plurality of NTC samples.

Alternate embodiments for defining an origin might not involve the uses of NTC samples. For example, the defined origin could be predefined based on previously obtained data. Another embodiment could use the morphology of the sample clusters to determine the origin. Yet another embodiment could be based on the use fluorescent data collected in early cycles, which may indicate an acceptable origin for the objective of defining an origin. Alternatively, as one of ordinary skill in the art is apprised, a baseline containing a defined origin for y=C, where C is a constant may be arbitrarily defined, based on a user-defined rationale, in which the line contains a user-defined origin for the data. For example, an origin could be selected as the origin of the graph as shown in FIG. 3, for which y=0 would provide a baseline. According to various embodiments, for step 20 of FIG. 1, an angle for each data point in the data set may be determined from a baseline including a determined or selected origin.

As depicted in step 30 of FIG. 1, for various embodiments of embodiments of methods and systems for the analysis of genotyping data of the present teachings, an optimal angle configuration search may be performed. According to various embodiments, an exhaustive search of angle configuration space may be conducted, in which the data set of data points for a plurality of samples can be fit to a best-fit angle configuration selected from a data base of angle configurations.

In principle, for K samples undergoing genotyping analysis for a diploid genome, there are $3^K$ possible genotype assignments, which typically may be too many to effectively search every possibility. According to systems and methods of the present teachings, a data base of angle configurations may be generated from which a search for a fit of data in a data set to an optimal angle configuration may be done. In various embodiments, data sets of genotyping data may be selected as training sets for generating a data base of angle configurations. According to various embodiments, a data base of angle configurations may include a probability of a particular angle configuration occurring, which is associated with each angle configuration in a data base. For various embodiments of systems and methods according to the present teachings, the probability of a particular angle configuration occurring can be estimated as a function of the frequency of occurrence of the particular angle configuration in a training set. For example, the probability of an angle configuration occurring can be estimated by evaluating the number of times the angle configuration occurs in a training set, divided by the total number of angle configurations in the training set.

Such data sets of genotyping data may be selected for having attributes representing genotyping data that may be analyzed using various embodiments of systems and methods for genotyping by angle configuration. Data sets used as training sets for generating a data base of angle configurations may have attributes derived from variables impacting such data sets, such as, but not limited by, the type of sample analyzed (i.e. a certain cell, tissue, or biological fluid type), the sample preparation method, assay conditions (i.e. probe, reporter, reagents and matrix), and instrumentation (i.e. detector, thermal block assembly, and sample block). Accordingly, training sets of data used to generate a data base of angle configurations may be selected to especially reflect the type of data being analyzed. In various embodiments, the angle configuration space may be defined by a user.

For example, various embodiments of the present teachings may utilize a data set of more than 100,000 genotyping assays that was selected for attributes for performing genotyping analysis as the basis for generating a data base of angle configurations from which the search for a fit of data in a data set to an optimal angle configuration may be done. Such a training set may be used to define the angle space from which a data base of angle configurations could be generated. For various embodiments of systems and methods of the present teachings, an angle configuration space may be defined in order to provide exhaustive searching to ensure, with an associated confidence, that a global fit of the samples to an angle configuration may be found. For example, instead of searching $3^K$ possible genotype assignments, using a selected training set of more than 100,000 genotyping assays in various embodiments, angle configuration space according to various embodiments of systems and methods of the present teachings was defined as:

$\alpha_1$ can vary between −47.5° and 92.5°
$\alpha_2$ can vary between −47.5° and 137.5°
$\alpha_3$ can vary between −2.5° and 137.5°
Angle spacing for each angle is 5°
Angles are in increasing order $\alpha_1 < \alpha_2 < \alpha_3$ Using the above boundary conditions derived from a training set of genotyping data having targeted attributes, a data base of angle configurations having an overall number of 3797 unique angle configurations can be generated. Additionally, for various embodiments of systems and methods of the present teachings, each unique angle configuration in a data base can be associated with a probability that the angle configuration may occur.

Various embodiments of a data base utilized in, for example, but not limited by, step 30 of FIG. 1, may vary according to how the angle configuration space may be defined by the selection of a training set of data. Accordingly, the number of angle configurations in a data base may be larger or smaller than 3797, depending on the selection of a training set. For example, the selection of a training set may impact how the ranges of the angles could be defined to create either more or less possible angle configurations than the 3797 unique angle configurations in the above example. The selection of a training set could alter the angle spacing to be more or less than 5°, which may also impact the number of angle configurations for various embodiments of an angle configuration data base. Additionally, the selection of a training set may impact the evaluation of a probability of any one angle configuration occurring in various embodiments of an angle configuration data base.

Regarding the selection of a training set, it may be desired to limit the data set to have a limited set of attributes derived from variables impacting such data sets so as to improve accuracy of the algorithm for those characteristics. For example, it may be desirable to select a data set from a single assay type to ensure the algorithm is optimized for that assay. For various embodiments of systems and method according to the present teachings, a unique set of angle configurations generated empirically from training sets can be stored in a data base. Such a data base can be designed to remain static (i.e. unchanged) for use with system and methods according to the present teachings, or may designed to be dynamically changing, and continually updated. According to various embodiments, a data base may be updated by an end user directly, or through an automated process. In various embodiments, new angle configurations can be added to a data base as a training set is updated with new data. For example, an angle configuration data base can be updated as more samples are run for the particular assay and added to a training set. In this regard, by the selection of a training set of data, various embodiments of an angle configuration data base may be generated, and may be uniquely created for use in evaluation of targeted assays and data sets.

Figure 7A:
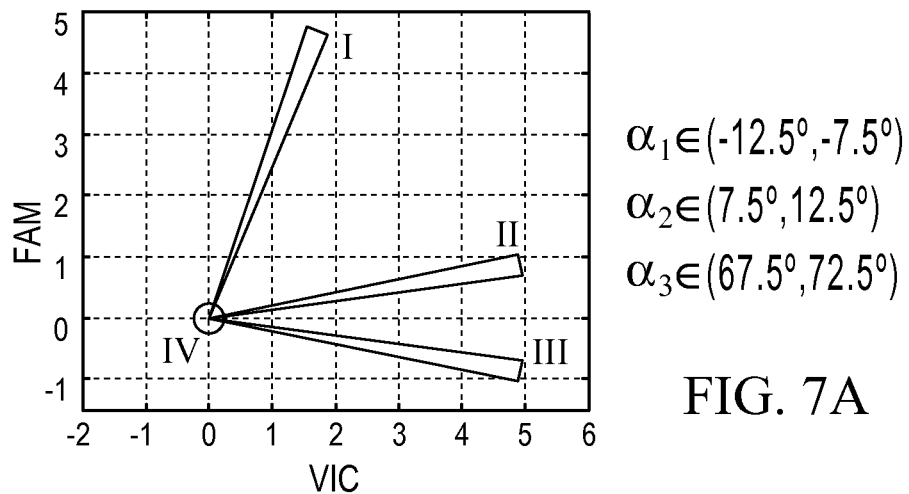
FIGS. 7A-7C are graphical representations of angle configurations that may be a subset of angle configurations according to various embodiments of a data base of angle configuration that are possible for genotyping data.
Figure 7B:
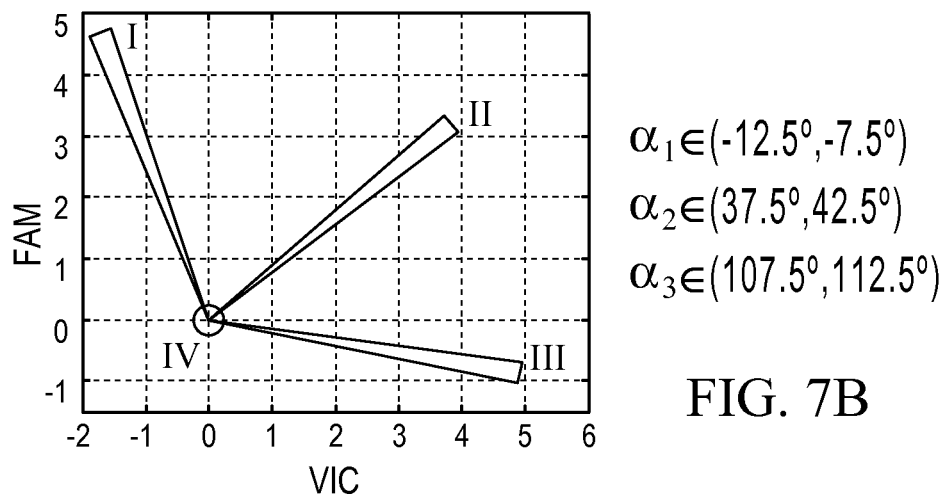
Figure 7C:
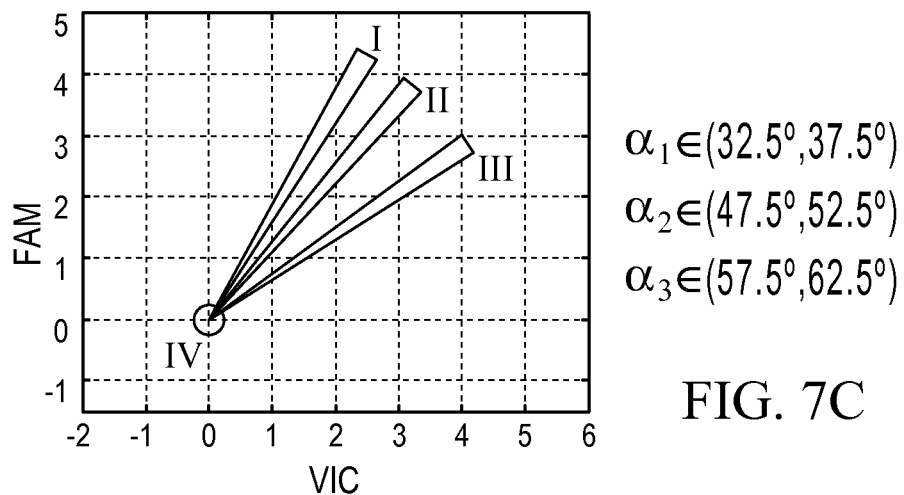

In FIGS. 7A-7C, three possible angle configurations according to various embodiments of an angle configuration data base are shown graphically, to assist in an understanding of various embodiments of conducting an optimal angle configuration search, as indicated in step 30 of FIG. 1. As indicated aside each figure, the three angles, and angle spacing for each exemplary angle configuration shown are consistent with various embodiments of an angle configuration data base, as given in above example. Though the angles are listed in degrees, as one of ordinary skill in the art would recognize, any form of angle representation may be used, such as radians or polar coordinates. In FIGS. 7A-7C, every exemplary angle of three discrete angles is listed in degrees, with an angle spacing of 5°, so that each angle configuration covers a unique portion of a defined angle configuration space.

Figure 8C:
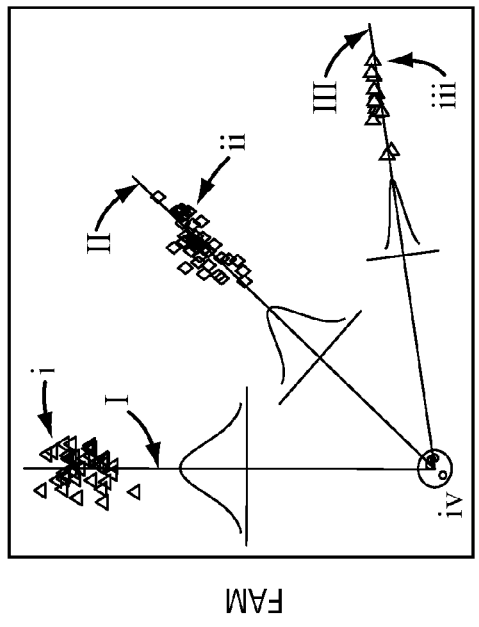
FIGS. 8A-8C are graphical representations of various embodiments of methods for the analysis of genotyping data.
Figure 8B:
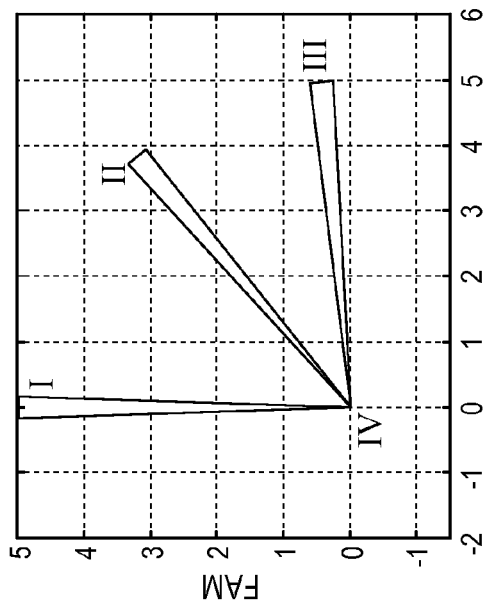
Figure 8A:
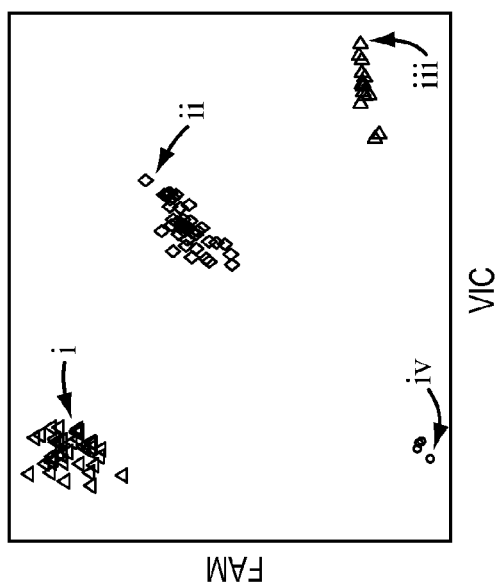
Figure 9C:
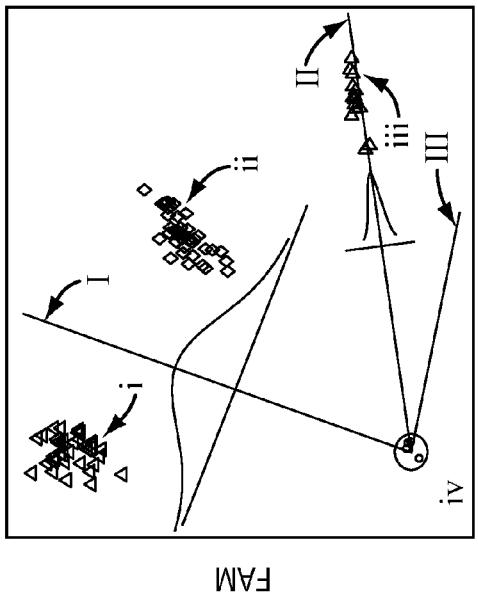
FIGS. 9A-9C are graphical representations of various embodiments of methods for the analysis of genotyping data.
Figure 9A:
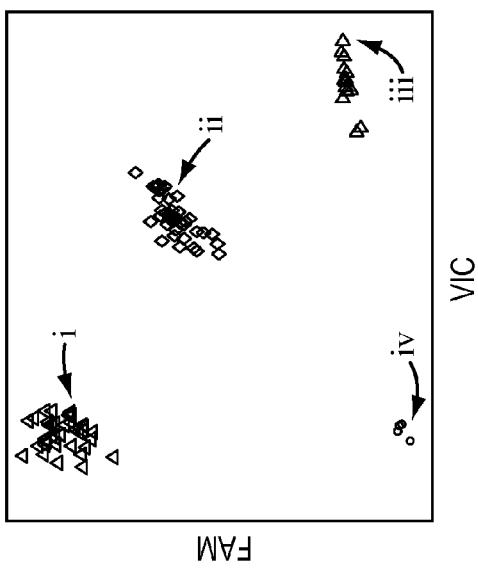
Figure 9B:
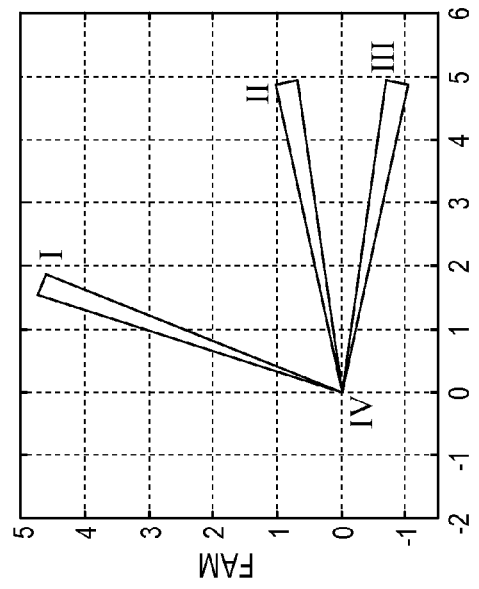

FIGS. 8A and 8B, and FIGS. 9A and 9B depict various embodiments of methods and systems for the analysis of genotyping data of the present teachings, as indicated in steps 10-30 of FIG. 1. In FIG. 8A, a data set of data points for a plurality of biological samples for a genotyping assay is depicted, as displayed as clusters i, ii, and iii in FIG. 8A. Additionally, a cluster iv is shown in FIG. 8A, which cluster may be used to determine a defined origin. As previously discussed, such a cluster may be a data set of data points from a non-template control (NTC) set of samples. In various embodiments of the present teachings, angles can be determined for each sample data point, where vertex IV for each angle, for example, but not limited by, as shown in FIGS. 8B and 8C, as well as FIGS. 9B and 9C, is a defined origin. In an iterative process, every sample may be assessed against a fit to an angle configuration in a data base, such as an angle configuration graphically displayed in FIG. 8B. As can be seen in FIG. 8C, the central lines I, II, and III of the angle configuration of FIG. 8B, appears to be a reasonable fit to the data. In contrast, in comparison to FIGS. 9A-9C, the angle configuration from the data base, as depicted in FIG. 9B, is not a good fit to the data of FIG. 9A, as is evident from inspection of FIG. 9C. As will be discussed in more detail subsequently, for various embodiments of methods and systems of the present teachings, a fit score including a term for the sum of the fit of all data points to an angle configuration in a data base may be calculated, and may be used to assess the fit of the data to an angle configuration in a data base.

The graphic depiction of various embodiments of method 100 of FIG. 1 is given in FIGS. 10A-10C and FIGS. 11A-11C. With each figure, a fit score is listed, wherein the fit score is defined as:

$$L_i = \Sigma L_{i,k} + L_{i,a\ priori} + L_{i,Hardy\ Weinberg}$$

where
$L_i$ is a total fit score for an angle configuration in an angle configuration data base.
$\Sigma L_{i,k}$ is a term in the total fit score that is a fit sum for all data points in a data set to an angle configuration in a data base.
$L_{i,a\ priori}$ is a term in the total fit score related to the probability that an angle configuration may occur and may be provided as information in an angle configuration data base.
$L_{i,Hardy\ Weinberg}$ is a term in the total fit score related to a fit of the data to a Hardy-Weinberg distribution.

According to various embodiments of methods and systems of the present teachings, the highest score for an angle configuration may be used to define a best-fit angle configuration. In various embodiments of systems and methods of the present teachings, additional terms beyond the terms generated using information in an angle configuration data base may be added to the fit score. For various embodiments, additional terms may utilize information, for example, but not limited by, the agreement of fit of an angle configuration with positive controls, with a specified allele frequency, and with a Hardy-Weinberg distribution as additional criteria of fit of an angle configuration to a data set. Any number of positive controls can be used. In some cases it may be beneficial to have one or more positive controls for one or more of the clusters. Furthermore, it may be desired to bias the fit score dynamically based on the type of positive control which would include but not be limited to synthetic positive controls and biological positive controls. Positive controls are typically data for which the genotype is known. However, this need not be the case. A positive control can be a non-biological fluorescent marker which still can be used to calculate the expected location of a cluster.

In one embodiment, the fit of data associated with sample "k" to angle configuration "i", $L_{i,k}$, is the logarithm of the probability of the angle of the data for sample "k" arising in an assay with true angle configuration "i". For example, this probability can be modeled as a mixture of normal distributions around the genotype angles comprising the angle configuration "i". In various embodiments, $L_{i,a\ priori}$ is a logarithmic expression of the probability for angle configuration "i". Such a probability may be associated with each angle configuration in a data base, as previously described. According to various embodiments of the present teachings, $L_{i,Hardy\ Weinberg}$ may be derived through a three step procedure. In a first step, a conditional genotype call can be assigned to each data point, by assuming that angle configuration "i" is a correct angle configuration. In a second step, frequencies of the three genotypes and the two alleles are calculated from the conditional genotype calls. Finally, in a third step, $L_{i,Hardy\ Weinberg}$ may be calculated as the logarithm of the p-value for the Pearson's chi-square test for fit of the distribution, which compares the observed frequencies of the three genotypes to Hardy-Weinberg genotype frequencies expected for a population with the observed allele frequencies.

Figure 10A:
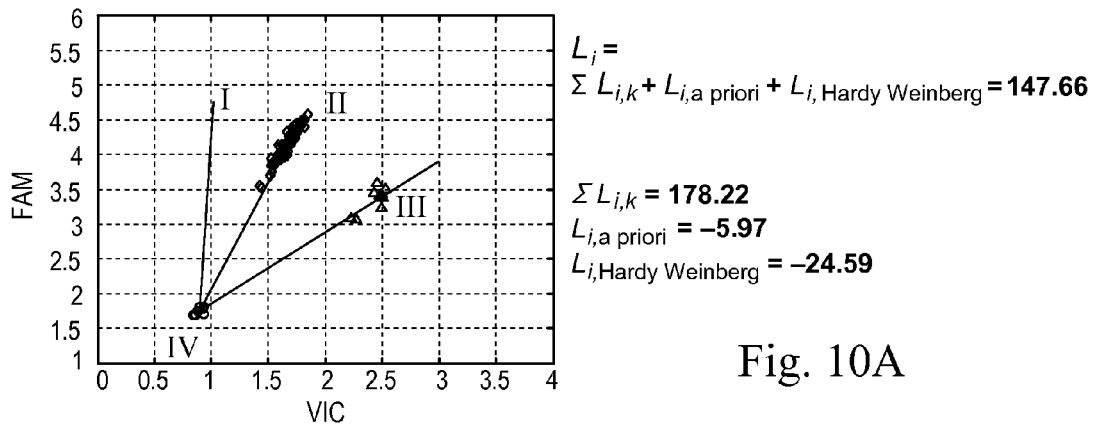
FIGS. 10A-10C are graphical representations of the fit of an exemplary two-cluster data set according to various embodiments of methods for the analysis of genotyping data.
Figure 10B:
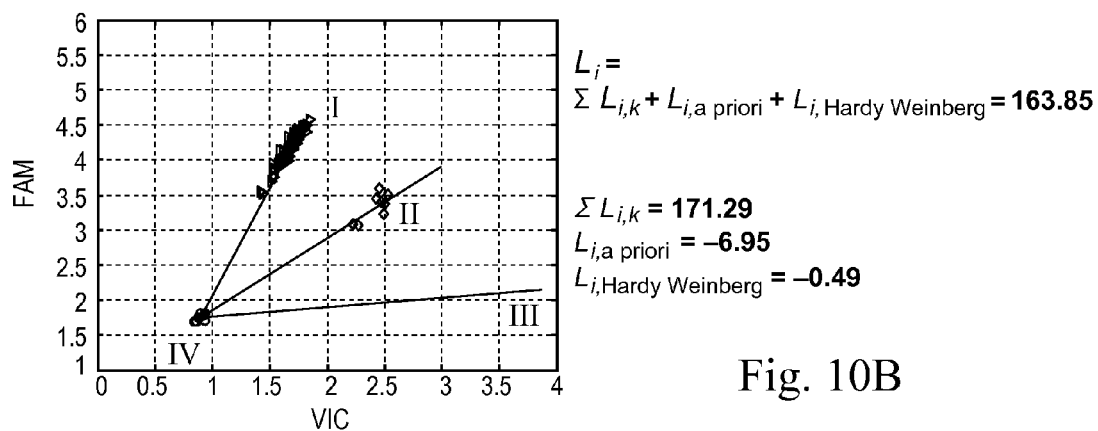
Figure 10C:
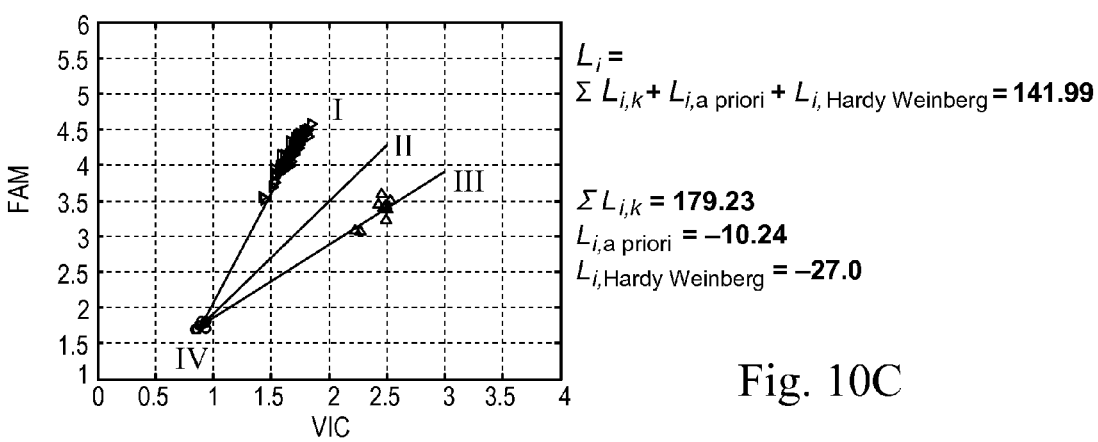
Figure 11A:
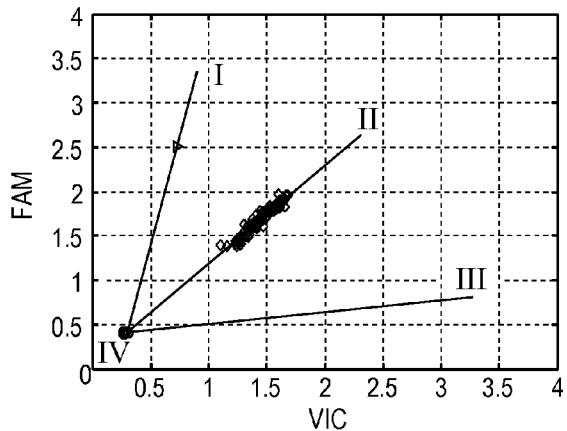
FIGS. 11A-11C are graphical representations of the fit of an exemplary one-cluster data set according to various embodiments of methods for the analysis of genotyping data.
Figure 11B:
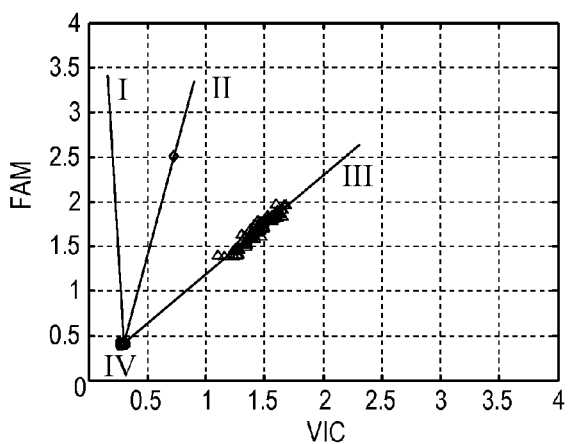
Figure 11C:
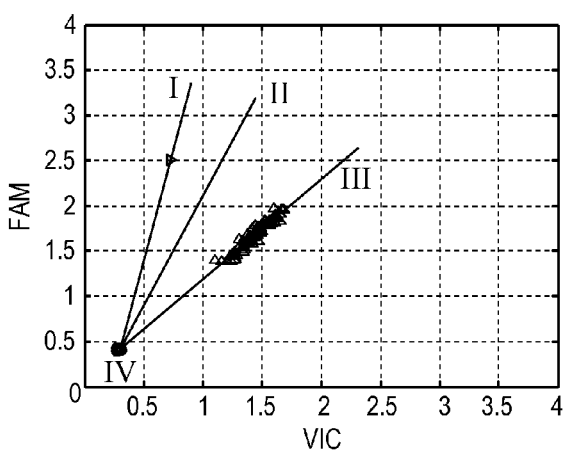

FIGS. 10A-10C and FIGS. 11A-11C depict examples of a fit of three different angle configurations to two different data sets of data points for a plurality of biological samples, according to various embodiments of methods 100 and 200 of the present teachings. In FIGS. 10A-10C, the graphic fit of the central angles of an angle configuration from a data base to the same data set is displayed, and an overall fit score is shown, along with the values of every term of the overall score. At a glance, the three angle configurations appear to be a reasonable fit, in contrast, for example, to the fit shown in FIG. 9C. It is apparent that with the Hardy-Weinberg fit score, that the angle configuration in FIG. 10B would be selected with the highest fit score. For this data set the angle configuration of FIG. 10B was validated as a correct fit to the data set. However, without that additional Hardy-Weinberg term, the angle configuration of FIG. 10A would have the highest score. FIGS. 11A-11C depict the fit of three different angle configurations to a data set of data points for a plurality of biological samples where there is only one cluster of data points in a data set. For the data set represented in this figure set, FIG. 11B was validated as a correct fit to the data set, which has the highest fit score.

As shown in step 40 of FIG. 1, an assignment of a final genotype classification to each sample in the plurality of sample may be done. According to various embodiments of methods and systems of the present teachings, the assignment of a genotype for each data point corresponding to each sample may be done, as each angle of the best-fit angle configuration may be discretely associated with one of the three possible allelic combinations defining a genotype classification. For example, in FIG. 3, a data point associated with angle $\alpha_3$ is in turn associated with a genotype homogeneous for the allele detected by the labeling probe of signal 1.

Regarding FIG. 1, step 50, as previously discussed, and as one of ordinary skill in the art may readily recognize, there are various ways of outputting genotyping information; for example, but not limited by genotyping data, final genotyping assignments, and genotyping quality scores, to an end user in numerous formats using numerous devices. For example, with respect to format of genotyping information, the data may be presented in a graphical format, as a written report, or combinations thereof. With respect to output devices, genotyping information may be output to devices such as, but not limited by a printer, a cathode ray tube (CRT) display, a liquid crystal display (LCD), and a light-emitting diode (LED) display.

Figure 2:
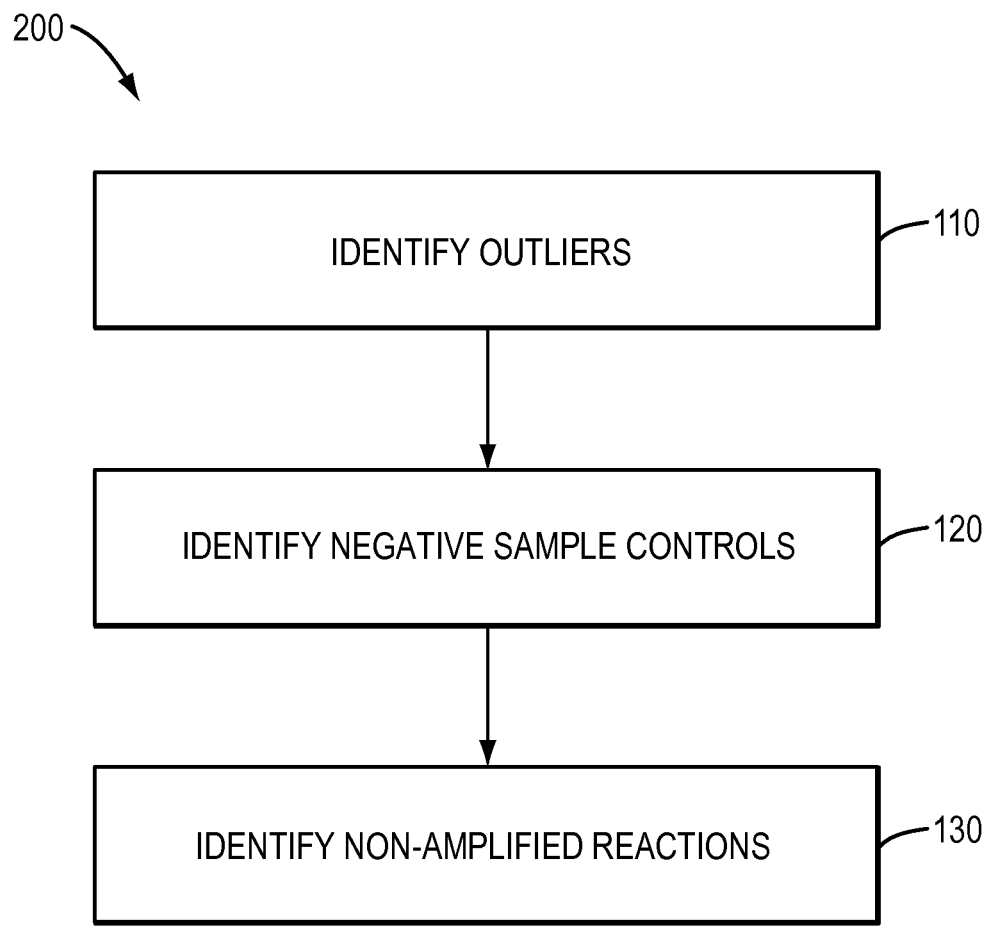
FIG. 2 is a flow chart that depicts various embodiments of methods for the pre-data analysis processing of genotyping data.

As depicted in FIG. 2 for method 200, steps 110-130, according to various embodiments of methods and systems for the analysis of genotyping data of the present teachings, preprocessing of the data may be done. In various embodiments, the preprocessing may be done before the determination of an angle for every data point in a data set.

According to various embodiments, as indicated in step 110 of method 200, outliers may be identified, and indicated as invalid. Recalling, in view of FIG. 3, every sample amplified using a first probe having a first signal and a second probe having a second signal may be plotted in a Cartesian coordinate system of signal 1 versus signal 2. In that regard, valid samples may have coordinates in 1 of three sets; (signal 1, signal 1), (signal 1, signal 2), or (signal 2, signal 2). For various embodiments, an outlier may be identified according to having coordinates that may deviate from one of the three expected sets. For example, but not limited by, in various embodiments, an outlier may be identified as invalid if it has essentially no signal for one coordinate. For various embodiments, an outlier may be called if the intensity of a sample is off scale for a detector reading. Yet another embodiment would be to define an outlier if the data point falls in an area not defined by an angle configuration. In various embodiments, this area could be based on calculated probabilities that a sample belongs to a genotype or alternatively could be calculated based on the Euclidean or Manhattan distance from the cluster centroids. Another embodiment allows multiple zones in the Cartesian coordinate system to be define arbitrarily which would be used to determine if a sample is an outlier. A radial zone centered at the origin and bounded by an inner radius and outer radius such that the inner and outer radius are between the genotype clusters and NTC cluster would be an example. Here the inner and outer radius could be calculated by, but not limited to, using probabilities or as mentioned before, defined arbitrarily.

As previously discussed, an angle may be determined for a data point in reference to a baseline. For various embodiments, a baseline may be determined using a non-template control (NTC), which are a negative sample control. According to various embodiments, as indicated in step 120 of method 200, shown in FIG. 2, for various embodiments of methods and systems of the present teachings, preprocessing the data would include a step of identifying the negative control samples. According to various embodiments, such negative controls may be designated as part of the assay set-up, and the information regarding the identity of negative samples may be stored in an accessible computer-readable location. For various embodiments, the NTC cluster may be identified, and a centroid of the cluster identified, which centroid may define an origin and baseline.

According to various embodiments as indicated in step 130 of method 200, a sample for which PCR has been inhibited may not have an appreciable signal amplitude, and may be fall within or near a NTC cluster. Accordingly, for various embodiments of step 130 of method 200, once the negative control cluster has been identified, biological samples for which amplification failed to occur may be identified accordingly. Additionally, for various embodiments, after step 120 of method 200 has been completed, it may be possible to identify invalid negative controls. For example, a negative control is not anticipated to have an appreciable signal amplitude. In various embodiments, all samples inputted as negative control having a signal amplitude greater than a defined signal amplitude may be defined as outlier NTCs, and identified as invalid. In the regard, one of ordinary skill in the art would recognize that the step of identifying outliers may occur according to when and how information about other samples is inputted. Therefore, for various embodiments, step 110 may reoccur as a preprocessing step.

For various embodiments of methods and systems for the analysis of genotyping data of the present teachings, a quality value may be assigned for every final genotype call assigned to every sample. A quality value may convey to an end user information about the likelihood that a correct genotype has been assigned to a given sample. As such, a quality value may be used as additional information for an end user to evaluate a genotype assignment for a sample. As one of ordinary skill in the art of genotyping analysis is apprised, a quality value could be expressed in probability scale, in percent, in phred scale, or any other unit.

According to various embodiments of systems and methods of the present teachings, a quality value for sample "k" can be obtained by first generating three genotype scores ($S_{1,k}$, $S_{2,k}$, $S_{3,k}$), one for each of the three possible genotypes. Each score is a measure of the likelihood that the sample "k" may be that genotype. For various embodiments, a quality value in probability scale can be calculated according to formula:

$$QV_k = \max(S_{1,k}, S_{2,k}, S_{3,k}) / (S_{1,k} + S_{2,k} + S_{3,k})$$

In various embodiments, the genotype score $S_{1,k}$ comprises a model-based probability that a typical sample with genotype 1 could have a signal angle equal to that observed for sample "k". It can also comprise a model-based probability that a typical sample with genotype 1 could have a signal magnitude equal to that observed for sample "k". Common probabilistic models for typical sample angles and magnitudes include normal distribution for sample angles (centered around the angle from the best angle configuration associated with genotype 1); normal or log-normal distribution for sample magnitudes. It is standard to estimate the missing parameters of these distributions from the sample signals and their assigned genotypes.

Alternatively, a quality value for a sample may be obtained from the distance from the cluster centroid or metrics derived from the cluster morphology. Furthermore, metrics such as the number of sigma separations between clusters can be used in obtaining a quality value.

While the principles of various embodiments of methods and systems for the analysis of genotyping data have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed is:

1. A non-transitory computer-readable medium encoded with instructions, executable by a processor, for determining a genotype for a genomic locus in a biological sample, the instructions comprising instructions for:
   receiving a data set for a genotyping assay, wherein the data set comprises a data point for each sample in a plurality of biological samples;
   determining an angle for each data point in the data set, wherein a vertex for each angle contains a defined origin;
   performing an optimal angle configuration search for the data set; said optimal angle configuration search comprising a best fit of the angles determined for each data point in the data set to an angle configuration in a plurality of angle configurations in a data base; and
   assigning a final genotype classification to each sample in the plurality of biological samples based on the fit of the data set to a best-fit angle configuration, wherein each angle of the best-fit angle configuration is discretely associated with a finite number of allelic combinations defining a genotype classification.

2. The computer-readable medium of claim 1, wherein the optimal angle configuration search comprising a best fit of the plurality of angles is expressed as a term in a fit score used to evaluate the best fit for the data set.

3. The computer-readable medium of claim 2, wherein the fit score used to evaluate the best fit for the data set further comprises a term for an assigned probability of occurrence for each angle configuration in the data base of angle configurations.

4. The computer-readable-medium of claim 3, wherein the term uses a logarithmic expression of the assigned probability.

5. The computer-readable medium of claim 2, wherein the fit score used to evaluate the best fit for the data set further comprises a term for a Hardy-Weinberg allele frequency.

6. The computer-readable medium of claim 1, wherein an identified baseline is a line containing the defined origin.

7. The computer-readable medium of claim 1, where the origin is defined by a non-template control sample.

8. The computer-readable medium of claim 1, wherein each angle configuration in the data base comprises three angles.

9. The computer-readable medium of claim 1, wherein the definable number of allelic combinations is three for a diploid organism.

10. The computer-readable medium of claim 1, wherein the data base of angle configurations is empirically derived from a data base of genotyping data.

11. The computer-readable medium of claim 10, wherein the data base of genotyping data is selected for inherent attributes relating to how genotyping data is generated.

12. The computer-readable medium of claim 1, further comprising a step of preprocessing the data.

13. The computer-readable medium of claim 12, wherein preprocessing the data comprises identifying outliers.

14. The computer-readable medium of claim 12, wherein preprocessing the data comprises identifying negative sample controls.

15. The computer-readable medium of claim 12, wherein preprocessing the data comprises identifying non-amplified samples.

16. The computer-readable medium of claim 1, further comprising a step of assigning a quality value to the final genotype classification of each sample.

17. A computer implemented method for determining a genotype for a genomic locus in a biological sample, the method comprising:
   receiving a data set for a genotyping assay, wherein the data set comprises a data point for each sample in a plurality of biological samples;
   processing the data set on a computer to determine the genotype for each sample in a biological, the processing comprising:
      determining an angle for each data point in the data set, wherein a vertex for each angle contains a defined origin;
      performing an optimal angle configuration search for the data set; said optimal angle configuration search comprising a best fit of the angles determined for each data point in the data set to an angle configuration in a plurality of angle configurations in a data base; and assigning a final genotype classification to each sample in the plurality of biological samples based on the fit of the data set to the best-fit angle configuration, wherein each angle of the best-fit angle configuration is discretely associated with a finite number of allelic combinations defining a genotype classification.

18. The method of claim 17, further comprising a step of preprocessing the data.

19. The method of claim 17, further comprising a step of assigning a quality value to the final genotype classification of each sample.

20. The method of claim 17, wherein the optimal angle configuration search comprising a best fit of the plurality of angles is expressed as a term in a fit score used to evaluate the best fit for the data set.

21. The method of claim 20, wherein the fit score used to evaluate the best fit for the data_set further comprises a term for an assigned probability of occurrence for each angle configuration in the data base of angle configurations.

22. The method of claim 20, wherein the fit score used to evaluate the best fit for the data_set further comprises a term for a Hardy-Weinberg allele frequency.

23. A system comprising:

a processor; and a memory in communication with the processor; the memory storing instructions for:

receiving by a processor a data set for a genotyping assay, wherein the data set comprises a data point for each sample in a plurality of biological samples;

determining an angle for each data point in the data set, wherein a vertex for each angle contains a defined origin;

performing an optimal angle configuration search for the data set; said optimal angle configuration search comprising a best fit of the angles determined for each data point in the data set to an angle configuration in a plurality of angle configurations in a data base; and assigning a final genotype classification to each sample in the plurality of biological samples based on the fit of the data set to a best-fit angle configuration, wherein each angle of the best-fit angle configuration is discretely associated with a finite number of possible allelic combinations defining a genotype classification.

* * * * *